(12) United States Patent
Dobrinsky et al.

(10) Patent No.: US 10,535,212 B2
(45) Date of Patent: Jan. 14, 2020

(54) ULTRAVIOLET FLUORESCENT AUTHENTICATION

(71) Applicant: Sensor Electronic Technology, Inc., Columbia, SC (US)

(72) Inventors: Alexander Dobrinsky, Silver Spring, MD (US); Michael Shur, Vienna, VA (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

(21) Appl. No.: 15/846,896

(22) Filed: Dec. 19, 2017

(65) Prior Publication Data

US 2018/0174389 A1 Jun. 21, 2018

Related U.S. Application Data

(60) Provisional application No. 62/436,283, filed on Dec. 19, 2016.

(51) Int. Cl.
*G07D 7/12* (2016.01)
*G01N 21/64* (2006.01)

(52) U.S. Cl.
CPC ............... *G07D 7/12* (2013.01); *G01N 21/64* (2013.01)

(58) Field of Classification Search
CPC .. G01N 2021/6421; G01N 21/64; G07D 7/12; G07D 7/1205; G07D 7/205
See application file for complete search history.

(56) References Cited

U.S. PATENT DOCUMENTS

| | | |
|---|---|---|
| 3,573,472 A | 4/1971 | Madalo |
| 4,146,792 A | 3/1979 | Stenzel et al. |
| 4,277,774 A | 7/1981 | Fujii et al. |
| 4,558,224 A | 12/1985 | Gober |
| 6,363,164 B1 * | 3/2002 | Jones ..................... G06K 9/033 382/135 |
| 7,031,566 B2 | 4/2006 | Kochergin et al. |
| 2002/0066543 A1 * | 6/2002 | Lilly ..................... B41M 3/144 162/140 |

\* cited by examiner

*Primary Examiner* — David P Porta
*Assistant Examiner* — Fani Boosalis
(74) *Attorney, Agent, or Firm* — LaBatt, LLC

(57) ABSTRACT

A solution for authenticating an article using a fluorescence signature emitted by the article in response to ultraviolet light is described. The article can include a light activated region that includes particles that can emit fluorescent radiation in response to being radiated with ultraviolet light. The light activated region can include one or more attributes for configuring the ultraviolet light and/or the fluorescent radiation to create the fluorescence signature. An authentication system can include an ultraviolet source, a fluorescent radiation sensor and components for operating each to acquire data used to authenticate the article.

20 Claims, 8 Drawing Sheets

ULTRAVIOLET FLUORESCENT AUTHENTICATION

REFERENCE TO RELATED APPLICATIONS

The current application claims the benefit of U.S. Provisional Application No. 62/436,283, filed on 19 Dec. 2016, which is hereby incorporated by reference.

TECHNICAL FIELD

The disclosure relates generally to authentication, and more particularly, to article authentication with ultraviolet fluorescence.

BACKGROUND ART

The counterfeiting of articles of many kinds is a serious worldwide problem, causing great loss of revenues to legitimate business, individuals, and governments. One approach to protect articles from counterfeiting is the incorporation of special markings that are difficult to reproduce but that enable easy detection. Examples are articles that are tagged or marked with identification marks that are printed using normally invisible chemicals, such as ultraviolet- or infrared-sensitive chemicals. Counterfeiters, however, have produced articles with similar hidden identification marks that are so sophisticated that only high performance scanners and laboratory equipment can distinguish the counterfeit article from the genuine article.

Many devices have been proposed to automatically determine authenticity of articles by detecting markings made with substances that are not normally visible in ordinary light, but become detectable by the devices when illuminated with non-visible radiation. One previous approach describes a label verification system in which each label to be verified is imaged onto a matrix of photocells, and an authentic label is imaged onto another matrix of photocells. Symbols on the labels preferably contain photoluminescent substances, and the matrix of photocells is provided with suitable filters, so that when the labels are illuminated with ultraviolet light, photocell responses are at a much higher degree of contrast.

Another approach discloses paper secured against forgery and a device for checking the authenticity of such papers. The paper carries materials that fluoresce in the visible, ultraviolet, or infrared spectral range in characteristic emission spectra. The device includes a light source for exciting fluorescent substances, a condenser lens concentrating the light emitted by the paper, a narrow band interference filter, a focusing lens, and a series of photocells arranged in the focal plane of the focusing lens. The outputs of the photocells are fed to a preamplifier and then to a comparator, and outputs of photocells are compared to establish the authenticity of the paper.

In still another approach, a currency discriminating apparatus is described, which utilizes the presence of a light-emitting substance in a printed zone of currency when irradiated with ultraviolet rays. The apparatus comprises an ultraviolet ray-emitting member, a photoelectric converter element, and a discriminating circuit for checking pattern signals.

Another illustrative approach discloses a counterfeit paper currency bill warning device that utilizes the characteristic fluorescence of genuine paper currency. In this device, an ultraviolet lamp illuminates the paper currency of unknown origin, and a sensor circuit responds to fluorescent radiation from the currency to give a signal to an indicator, which displays an indication of the fluorescence of the unknown paper currency relative to the fluorescence of genuine paper currency. The sensor is a photoresistor and the indicator is a variable intensity light or a digital display.

SUMMARY OF THE INVENTION

Embodiments of the invention described herein relate to a solution that facilitates authentication of genuine articles and discrimination of genuine articles from counterfeit articles. Unlike prior approaches, the inventors propose an authentication solution that can utilize narrow bandwidth ultraviolet solid state light emitting sources, which can be used in combination with a new design for a light activated region of the article to be authenticated, such as a document. The light activated region can include various features, which make counterfeiting the article more difficult than previous approaches. For example, the light activated region can comprise two or more layers, with attributes of each layer contributing to the authentication signature for the article. These attributes can include the thickness and composition of a layer, a distribution of and material forming fluorescent particles (e.g., nanoparticles) embedded in a layer, and/or the like.

Aspects of the invention provide a solution for authenticating an article using a fluorescence signature emitted by the article in response to ultraviolet light. The article can include a light activated region that includes particles that can emit fluorescent radiation in response to being radiated with ultraviolet light. The light activated region can include one or more attributes for configuring the ultraviolet light and/or the fluorescent radiation to create the fluorescence signature. An authentication system can include an ultraviolet source, a fluorescent radiation sensor and components for operating each to acquire data used to authenticate the article.

A first aspect of the invention provides an article comprising: a light activated region having a fluorescence signature with a plurality of attributes enabling authentication of the article, the light activated region comprising: a first layer including a plurality of particles, wherein the plurality of particles are configured to emit fluorescent radiation in response to being radiated with ultraviolet radiation; and a second layer immediately adjacent to the first layer, wherein the second layer is transparent to both the fluorescent radiation and the ultraviolet radiation and is stable and inert to an ambient environment within which the article is configured for use.

A second aspect of the invention provides an authentication system comprising: a data acquisition component including: an ultraviolet source; and a fluorescence sensor; and means for authenticating an article using the data acquisition component, wherein the means for authenticating performs the acts of: illuminating a surface of the article with ultraviolet radiation emitted by the ultraviolet source, the ultraviolet radiation having a first set of properties; acquiring, using the fluorescence sensor, data corresponding to fluorescence emitted from the article in response to the illuminating; and evaluating an authenticity of the article using the data corresponding to the fluorescence.

A third aspect of the invention provides a system for authenticating an article, the system comprising: an article configured for authentication using a fluorescence signature emitted in response to ultraviolet light, the article including: a substrate storing information; and a light activated region located on at least a portion of a first surface of the substrate, the light activated region including: a first layer including a plurality of particles, wherein the plurality of particles are configured to emit fluorescent radiation in response to being radiated with ultraviolet radiation; and a second layer immediately adjacent to the first layer, wherein the second layer is transparent to both the fluorescent radiation and the ultraviolet radiation and is stable and inert to an ambient environment within which the article is configured for use.

Other aspects of the invention provide methods, systems, program products, and methods of using and generating each, which include and/or implement some or all of the actions described herein. The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIG. 2A shows a cross-section of an illustrative article including a light activated region according to an embodiment, while

FIG. 3A shows a cross-section of another illustrative light activated region according to an embodiment, while

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a solution for authenticating an article using a fluorescence signature emitted by the article in response to ultraviolet light. The article can include a light activated region that includes particles that can emit fluorescent radiation in response to being radiated with ultraviolet light. The light activated region can include one or more attributes for configuring the ultraviolet light and/or the fluorescent radiation to create the fluorescence signature. An authentication system can include an ultraviolet source, a fluorescent radiation sensor and components for operating each to acquire data used to authenticate the article.

It is understood that, unless otherwise specified, each value is approximate and each range of values included herein is inclusive of the end values defining the range. As used herein, unless otherwise noted, the term "approximately" is inclusive of values within +/−ten percent of the stated value, while the term "substantially" is inclusive of values within +/−five percent of the stated value. Unless otherwise stated, two values are "similar" when the smaller value is within +/−twenty-five percent of the larger value. The description herein describes the use of fluorescence in authenticating an article. It is understood that fluorescence as used herein is inclusive of phosphorescence and phosphorescent materials are included in the description of fluorescent materials.

As also used herein, a layer is a transparent layer when the layer allows at least ten percent of radiation having a target wavelength, which is radiated at a normal incidence to an interface of the layer, to pass there through. Furthermore, as used herein, a layer is a reflective layer when the layer reflects at least ten percent of radiation having a target wavelength, which is radiated at a normal incidence to an interface of the layer. In an embodiment, the target wavelength of the radiation corresponds to a wavelength of radiation emitted or sensed (e.g., peak wavelength +/−five nanometers) by an active region of an optoelectronic device during operation of the device. For a given layer, the wavelength can be measured in a material of consideration and can depend on a refractive index of the material.

Figure 1:
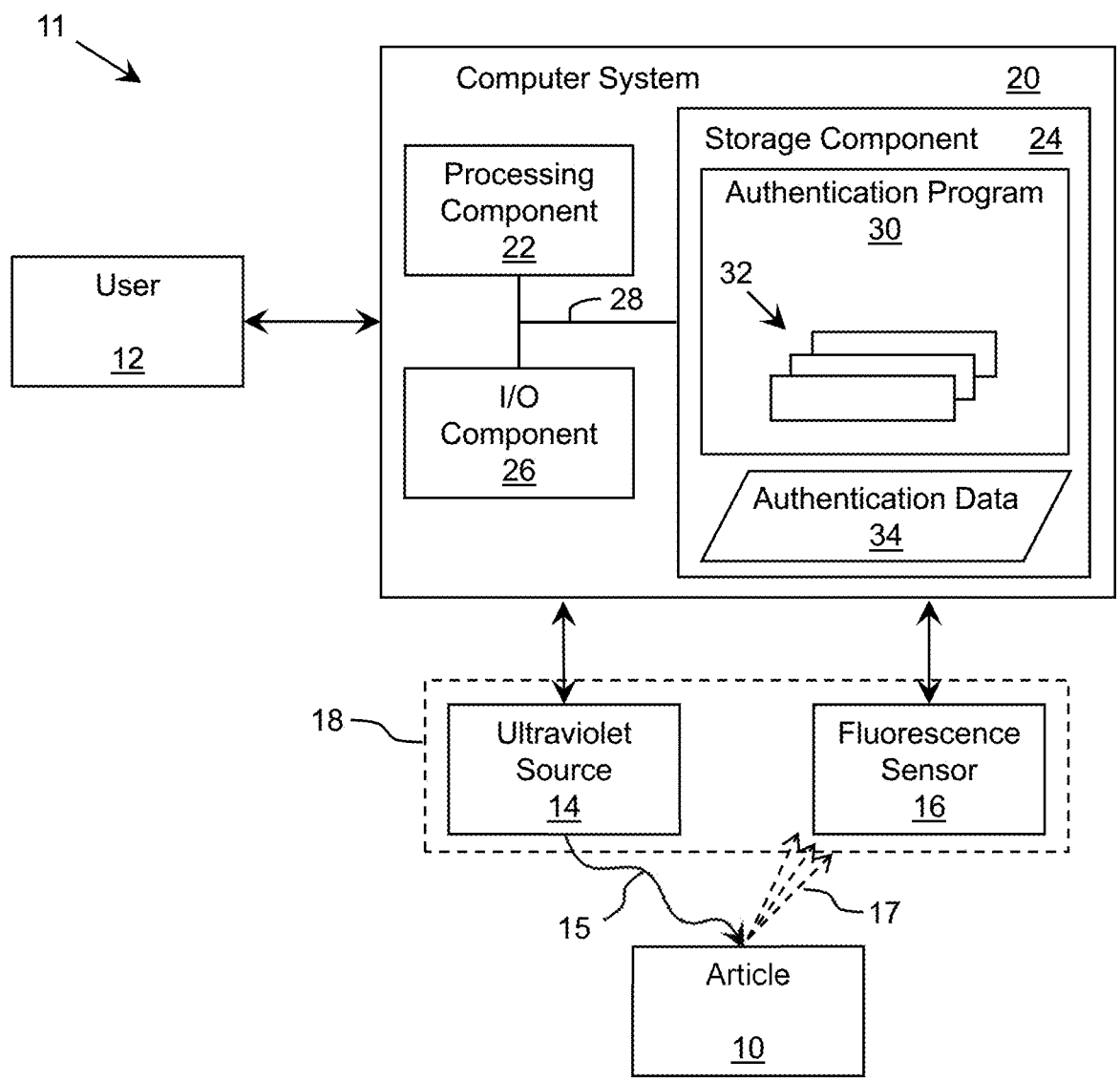
FIG. 1 shows an illustrative environment for authenticating an article according to an embodiment.

Turning to the drawings, FIG. 1 shows an illustrative environment 11 for authenticating an article 10 according to an embodiment. To this extent, the environment 11 includes a computer system 20 that can perform a process described herein in order to authenticate the article 10 using ultraviolet light 15 and the resulting fluorescence 17. In particular, the computer system 20 is shown including an authentication program 30, which makes the computer system 20 operable to authenticate the article 10 by performing a process described herein.

The computer system 20 is shown including a processing component 22 (e.g., one or more processors), a storage component 24 (e.g., a storage hierarchy), an input/output (I/O) component 26 (e.g., one or more I/O interfaces and/or devices), and a communications pathway 28. In general, the processing component 22 executes program code, such as the authentication program 30, which is at least partially fixed in storage component 24. While executing program code, the processing component 22 can process data, which can result in reading and/or writing transformed data, such as authentication data 34, from/to the storage component 24 and/or the I/O component 26 for further processing. The pathway 28 provides a communications link between each of the components in the computer system 20. The I/O component 26 can comprise one or more human I/O devices, which enable a human user 12 to interact with the computer system 20 and/or one or more communications devices to enable a system user 12 to communicate with the computer system 20 using any type of communications link. To this extent, the authentication program 30 can manage a set of interfaces (e.g., graphical user interface(s), application program interface, and/or the like) that enable human and/or system users 12 to interact with the computer system 20. Furthermore, the authentication program 30 can manage (e.g., store, retrieve, create, manipulate, organize, present, etc.) the data, such as authentication data 34, using any solution.

In any event, the computer system 20 can comprise one or more general purpose computing articles of manufacture (e.g., computing devices) capable of executing program code, such as the authentication program 30, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, the authentication program 30 can be embodied as any combination of system software and/or application software.

Furthermore, the authentication program 30 can be implemented using a set of modules 32. In this case, a module 32 can enable the computer system 20 to perform a set of tasks used by the authentication program 30, and can be separately developed and/or implemented apart from other portions of the authentication program 30. As used herein, the term "component" means any configuration of hardware, with or without software, which implements the functionality described in conjunction therewith using any solution, while the term "module" means program code that enables a computer system 20 to implement the actions described in conjunction therewith using any solution. When fixed in a storage component 24 of a computer system 20 that includes a processing component 22, a module is a substantial portion of a component that implements the actions. Regardless, it is understood that two or more components, modules, and/or systems may share some/all of their respective hardware and/or software. Furthermore, it is understood that some of the functionality discussed herein may not be implemented or additional functionality may be included as part of the computer system 20.

When the computer system 20 comprises multiple computing devices, each computing device can have only a portion of the authentication program 30 fixed thereon (e.g., one or more modules 32). However, it is understood that the computer system 20 and the authentication program 30 are only representative of various possible equivalent computer systems that may perform a process described herein. To this extent, in other embodiments, the functionality provided by the computer system 20 and the authentication program 30 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 20 includes multiple computing devices, the computing devices can communicate over any type of communications link. Furthermore, while performing a process described herein, the computer system 20 can communicate with one or more other devices and/or computer systems using any type of communications link. In either case, the communications link can comprise any combination of various types of optical fiber, wired, and/or wireless links; comprise any combination of one or more types of networks; and/or utilize any combination of various types of transmission techniques and protocols.

As discussed herein, the authentication program 30 enables the computer system 20 to authenticate an article 10 by performing a process described herein. In particular, the computer system 20, as directed by the authentication program 30, can acquire data regarding the article 10 by operating a data acquisition component 18. The data acquisition component 18 can include any of various combinations of I/O devices to acquire data regarding the article 10, which can be used to authenticate the article 10. Such data can include a visual appearance of the article 10, a size of the article 10, one or more watermarks present on the article 10, and/or the like.

Additionally, the article 10 can include a light activated region, which reacts to being illuminated by ultraviolet light, e.g., by emitting fluorescent radiation. To this extent, the data acquisition component 18 can include an ultraviolet source 14 and a fluorescence sensor 16. The computer system 20 can operate the ultraviolet source 14 to direct ultraviolet radiation 15 towards a region of a surface of an article 10, which corresponds to the light activated region of an authentic article, and operate the fluorescence sensor 16 to acquire data corresponding to fluorescence 17 emitted from the article 10, which can be stored as authentication data 34.

The ultraviolet (UV) source 14 can comprise any combination of one or more ultraviolet radiation emitters. When the UV source 14 includes multiple emitters, the emitters can include one or more types of emitters. For example, the UV source 14 can include a high intensity ultraviolet lamp (e.g., a high intensity mercury lamp), an ultraviolet light emitting diode (LED), and/or the like. In an embodiment, the UV source 14 includes a set of light emitting diodes manufactured with one or more layers of materials selected from the group-III nitride material system (e.g., $Al_xIn_yGa_{1-x-y}N$, where $0 \leq x$, $y \leq 1$, and $x+y \leq 1$ and/or alloys thereof). Additionally, the UV source 14 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like, toward the article 10. Illustrative wave guiding structures include, but are not limited to, a plurality of ultraviolet fibers, each of which terminates at an opening, a diffuser, and/or the like. When the UV source 14 includes multiple ultraviolet radiation emitters, the computer system 20 can independently control each ultraviolet radiation emitter and/or control the ultraviolet radiation emitters as a single group or multiple groups.

The fluorescent sensor 16 can comprise any combination of one or more fluorescent sensing devices. When the fluorescent sensor 16 includes multiple sensing devices, the sensing devices can include one or more types of sensing devices. In an embodiment, the fluorescence is discernible in one or more of visible light, ultraviolet light, or infrared light. To this extent, the fluorescent sensor 16 can comprise any type of sensor(s) sensitive to radiation corresponding to the fluorescence. For example, the fluorescent sensor 16 can include a visible camera, one or more photodetectors, and/or the like. The fluorescent sensor 16 can be configured to acquire data corresponding to a fluorescent power spectra distribution emitted by the article 10 in response to being illuminated by the ultraviolet radiation 15. To this extent, the fluorescent sensor 16 can be configured to acquire and store fluorescence data corresponding to the fluorescence of a two-dimensional region of the article 10 corresponding to a light activated region of an authentic article. Additionally, the fluorescence data can include data corresponding to variations in the peak fluorescent wavelengths and the magnitudes of the peak fluorescent wavelengths for the two-dimensional region of the article 10. To this extent, a fluorescent sensor 16 can comprise an imaging device with sensors sensitive to one or more of visible light, infrared light, and ultraviolet light, which is capable of acquiring a two dimensional image of the light activated region.

Regardless, operation of the ultraviolet source 14 to illuminate a surface of an article 10 to be authenticated and fluorescence sensor 16 to acquire data corresponding to the resulting fluorescence 17 of the article 10 can result in the acquisition of fluorescence signature data for the article by the computer system 20, which can be stored as authentication data 34. The fluorescence signature data can further include the fluorescence data acquired for the article 10 over a period of time during and/or after illumination by the ultraviolet source 14. Still further, the fluorescence signature data can include one or more attributes of the ultraviolet radiation that induced the emission of fluorescent radiation (e.g., peak wavelength, dose, exposed area, and/or the like). To this extent, an embodiment of the fluorescence signature data for an article 10 can include spatial, magnitude, wavelength, and time dimensions, for the fluorescent radiation 17 and/or for the ultraviolet radiation 15 used to induce the fluorescent radiation. Furthermore, an embodiment of the fluorescent sensor 16 can be configured to acquire a series of images (e.g., video) over the period of time. However, it is understood that embodiments of the authentication system described herein can perform authentication using fluorescence signature data that only includes a subset of these dimensions.

In an embodiment, the computer system 20 can store a target fluorescence signature as authentication data 34. Similar to the fluorescence signature data, an embodiment of the target fluorescence signature can include data defining target spatial, magnitude, wavelength, and time dimensions of a fluorescence signature for an authentic article. The target fluorescence signature can further define an acceptable variance for each of the attributes of the target fluorescence signature. The acceptable variance can vary widely based on attributes of the article and its intended use. A suitable acceptable variance for each attribute can be determined, for example, empirically, through analysis of known authentic articles after exposure to different conditions to which an article is anticipated to experience during use.

Regardless, the computer system 20 can compare the fluorescence signature data acquired for the article 10 to the target fluorescence signature to evaluate an authenticity of the article 10. It is understood that additional data can be used to determine the authenticity. For example, the computer system 20 can determine and compare one or more visible or physical attributes (e.g., including size, weight, and/or the like) of the article 10 to known attributes of an authentic article 10. Once an authenticity of the article 10 is determined, the computer system 20 can communicate the result to the user 12 (FIG. 1), which can be instructed as to further actions. For example, in the event the analysis indicates the article 10 is not authentic, the user 12 can be instructed to clean the light activated region and try to authenticate the article again, confiscate, destroy, or reject the article 10, and/or the like.

Figure 2A:
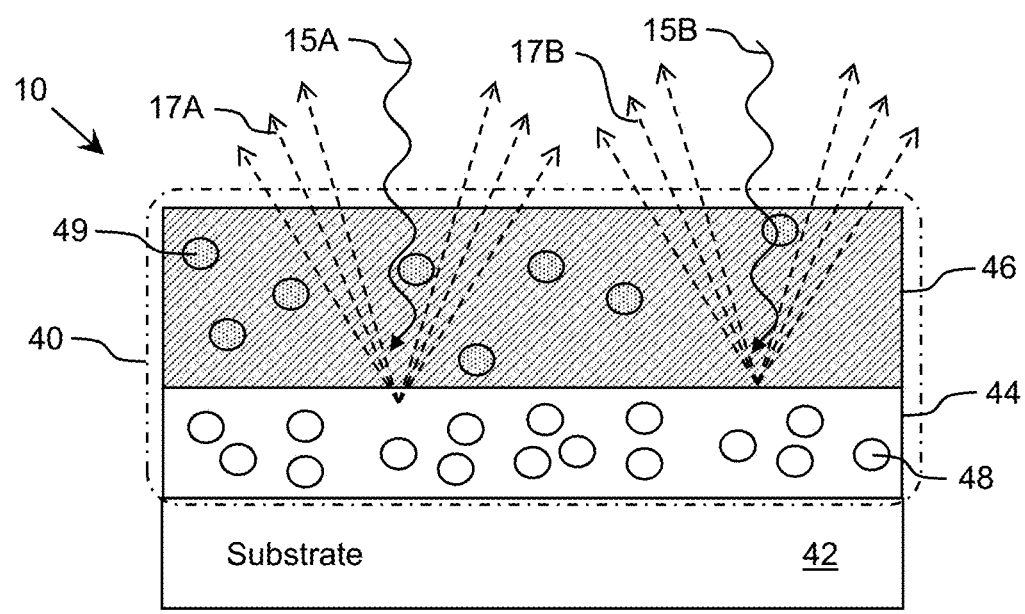

An embodiment of the invention provides an article 10 configured for authentication using ultraviolet light 15 and fluorescence 17, such as within the environment 11 shown in FIG. 1. To this extent, FIG. 2A shows a cross-section of an illustrative article 10 including a light activated region 40 according to an embodiment. It is understood that the article 10 is only illustrative of various articles that can be configured and utilized as described herein. Additionally, it is understood that an article described herein can have any shape or dimension. To this extent, embodiments of an article described herein are not limited to the shape and dimension of the article 10 shown in FIG. 2A. Furthermore, a light activated region 40 can correspond to an entire surface of the article 10 or only a portion of a surface of the article 10. For example, a light activated region 40 can correspond to a portion of an article and have a regular or irregular shape. The shape can correspond to, for example, a symbol or group of symbols.

Regardless, the article 10 is shown including a substrate 42, on which the light activated region 40 is located. The substrate 42 can correspond to any type of article for which authentication may be desired. In general, at least one surface of the substrate 42 includes information that is presented to a person viewing the article 10. Additionally, the substrate 42 can include one or more mechanisms for storing and providing information to a computer system (e.g., a magnetic stripe, a chip, a radio frequency identification device, a one or two-dimensional barcode, etc.). Regardless, the information stored using the substrate 42 is desired for verification and authentication. For example, the substrate 42 can correspond to a page of a legal document (e.g. a signature page), currency, a payment card, artwork, a government-issued identification card (e.g., passport, driver's license, non-driver ID), and/or the like.

The light activated region 40 can be located on either a front or back surface of the substrate 42. While the light activated region 40 is shown only on a single surface of the substrate 42, it is understood that an article 10 can include light activated regions 40 located on both surfaces of the substrate 42. While the light activated region 40 is shown as having a thickness greater than that of the substrate 42, it is understood that this is only to illustrate certain features of the invention. In an embodiment, the substrate 42 will have a thickness that greatly exceeds that of the light activated region 40. However, it is understood that embodiments of an article 10 can be implemented without a substrate 42. In this case, the light activated region 40 can correspond to the article to be authenticated.

The light activated region 40 can be applied to the surface of the substrate 42 using any solution. For example, the layer(s) of the light activated region 40 described herein can be fabricated directly on the surface of the substrate 42 using any solution. In an embodiment, the light activated region 40 can be adhered to a previously fabricated substrate 42 using any solution. The substrate 42 can be formed of any suitable material used to fabricate an article requiring authentication. Illustrative materials include paper, fabric, plastic, etc. When utilized, the adhesive can comprise an appropriate chemical that can adhere to the surface of the substrate 42 and the light activated region 40, such as ink, for example.

Regardless, the light activated region 40 is shown including a first layer 44 and a second layer 46. In an embodiment, both the first layer 44 and second layer 46 are formed of materials that are transparent to visible light. In this case, the light activated region 40 can be configured so as to not interfere with use of a surface of the substrate 42 corresponding to the light activated region 40 to convey information to an individual. The first layer 44 can comprise a thin film of material. For example, the first layer 44 can comprise any material that can fluoresce under UV radiation at a selected wavelength or range of wavelengths. For example, such a layer can comprise a light transparent polymer with fluorescent particles embedded therein. In one example, the layer can comprise an ink visible to a human that also contains fluorescent material (e.g., particles) capable of fluorescence under UV radiation at the selected wavelength.

The first layer 44 can include a plurality of particles 48, each of which is configured to emit fluorescent radiation in response to being illuminated with ultraviolet radiation of a particular range of wavelengths. In an embodiment, the particles 48 are nanoparticles, for which the largest dimension is less than 1,000 nanometers. However, it is understood that embodiments of the particles 48 can be larger. Additionally, it is understood that the first layer 44 can include particles 48 of different dimensions and/or different materials. The different materials and/or different sized of the particles 48 can result in different fluorescent radiation, e.g., emitting fluorescent radiation in response to ultraviolet radiation of different wavelengths and/or having differing fluorescence signatures in response to being exposed to the same ultraviolet radiation.

The particles 48 can be formed of any material that fluoresces in response to being exposed to ultraviolet radiation. In an embodiment, the first layer 44 includes particles 48 fabricated from a group III nitride semiconductor material including phosphorus. In an embodiment, the particles 48 can comprise a fluorescent dye, such as anthracene, quinine, etc., inorganic fluorescent phosphorous, such as $Tb^{3+}$ $LaPO_4$, and/or the like.

The second layer 46 can comprise a material that is stable and inert to an ambient environment within which the article is configured for use. As used herein, a material is stable to ambient conditions when the material does not significantly change its properties over an intended lifetime of use of the article 10, and more particularly the light activated region 40, due to interaction with the ambient environment within which the article 10 is intended for use. Such an ambient environment can comprise for example, exposure to air and/or water, as well as temperatures up to fifty degrees Celsius. While not shown for clarity, it is understood that the second layer 46 can extend beyond the first layer 44 to completely encapsulate and prevent exposure of the first layer 44 to the ambient environment. To this extent, the second layer 46 can directly contact the substrate 42 in areas surrounding the first layer 44. Additionally, the second layer 46 can have good adhesive properties for adhering to the first layer 44 and/or the substrate 42. Illustrative materials for the second layer 46 include a fluoropolymer, such as EFEP (a terpolymer composed of ethylene, tetrafluoroethylene (TFE), and hexafluoropropylene (HFP)), an amorphous fluoropolymer with high light transparency (e.g., CYTOP® sold by Bellex International Corporation), and/or the like.

The second layer 46 can be configured to control an intensity and/or distribution of the fluorescent radiation emitted from the light activated region 40. In an embodiment, small changes to a thickness of the second layer 46 can significantly affect the fluorescent radiation 17A, 17B emitted from the light activated region 40 when the small changes affect the absorption or scattering of UV light by the second layer 46. For instance, the second layer 46 can be transparent to visible radiation such as fluorescent radiation. To this extent, a thickness of the second layer 46 can be precisely controlled. For example, the thickness of the second layer 46 can be controlled to within 100 nanometers. In an embodiment, the thickness of the second layer 46 is in a range between twenty millimeters and two hundred nanometers.

Additionally, the second layer 46 can have controlled transparent properties of the ultraviolet radiation 15A, 15B and/or fluorescent radiation 17A, 17B. For example, the second layer 46 can be formed of a material having a sharp transparency cutoff at a wavelength smaller (or larger) than a peak wavelength of ultraviolet radiation 15A, 15B. In a more particular embodiment, the transparency cutoff is approximately twenty nanometers less than the smaller peak wavelength of the ultraviolet radiation 15A, 15B. For instance, the material can comprise a fluoropolymer with a sharp transparency cutoff. In an embodiment, the material can comprise $SiO_2$, a semiconductor layer having a specific absorption edge, and/or the like. In another more particular embodiment, the second layer 46 can be formed of a material having multiple transparency regions and intervening absorption peaks within the ultraviolet spectrum. In this case, the peak wavelengths for the ultraviolet radiation 15A, 15B can be selected to match the transparency regions of the second layer 46. In an embodiment, the material can comprise a polymer, such as photochromic polyurethanes, which may be transparent around 250 and 400 nm but absorbing at 200 and 300 nm.

In an embodiment, a transparency of the second layer 46 can be polarization dependent. For instance, the second layer 46 can comprise a film having nanoparticles or nano-objects that interact differently with light of different polarization. As an example, the second layer 46 can include carbon nanotubes embedded in a film, which can absorb ultraviolet light differently depending on the polarization. Similarly, ultraviolet polarizers are known in art, such as a macroporous silicon (MPSi).

Additionally, the second layer 46 can have controlled scattering properties of the ultraviolet radiation 15A, 15B and/or fluorescent radiation 17A, 17B. For example, the second layer 46 can be configured to scatter the fluorescent radiation 17A, 17B to result in a particular polar distribution for the fluorescent radiation 17A, 17B. For example, the second layer 46 can include a plurality of particles 49 (e.g., nanoparticles), which have scattering properties for the fluorescent radiation 17A, 17B. In this case, the density of the particles 49, which can be reflective or transparent to fluorescent radiation, within the second layer 46 relates to a degree of scattering of the fluorescent light. Illustrative materials for the particles 49 include aluminum oxide ($Al_2O_3$), silicon dioxide ($SiO_2$), and/or the like.

As illustrated, a surface of the light activated region 40 can be irradiated with radiation 15A, 15B, which can result in emission of fluorescence 17A, 17B from the light activated region 40. In an embodiment, the radiation 15A, 15B can have different peak wavelengths. For example, the radiation 15A, 15B can be generated by different narrow band light sources, such as ultraviolet LEDs, for which a difference between the peak radiation wavelengths of the light generated by the light sources exceeds the FWHM for the radiation 15A, 15B. In an embodiment, the radiation 15A, 15B have FWHMs of 20 nanometers or less. In an embodiment, at least one of the radiation 15A, 15B has a peak wavelength in a range of 250 to 350 nanometers.

Figure 2B:
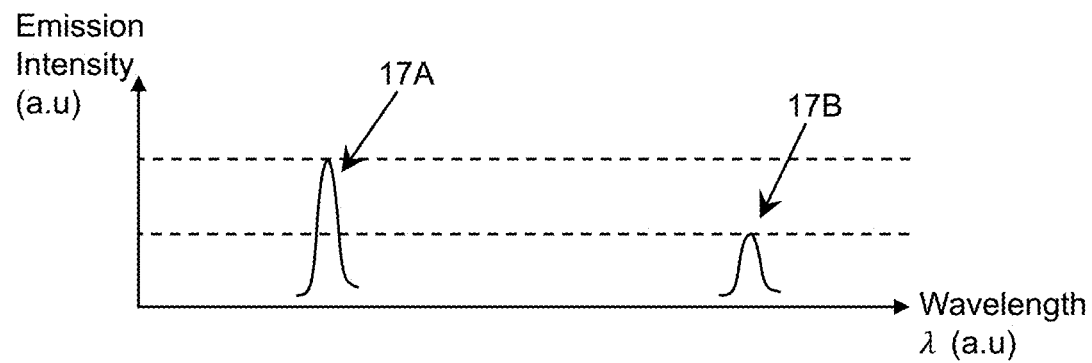
FIG. 2B shows attributes of fluorescent radiation emitted by the light activated region according to an embodiment.

The use of radiation 15A, 15B with different peak wavelengths can result in fluorescent radiation 17A, 17B with one or more attributes that differ. For example, as illustrated in FIG. 2B, the fluorescent radiation 17A, 17B can have different amplitudes and/or wavelengths that can depend on the radiation 15A, 15B used to irradiate the light activated region 40. The differences in the fluorescent radiation 17A, 17B can be sufficiently significant to enable distinction between the fluorescent radiation 17A, 17B when measured using, for example, an authentication system described herein.

Figure 3A:
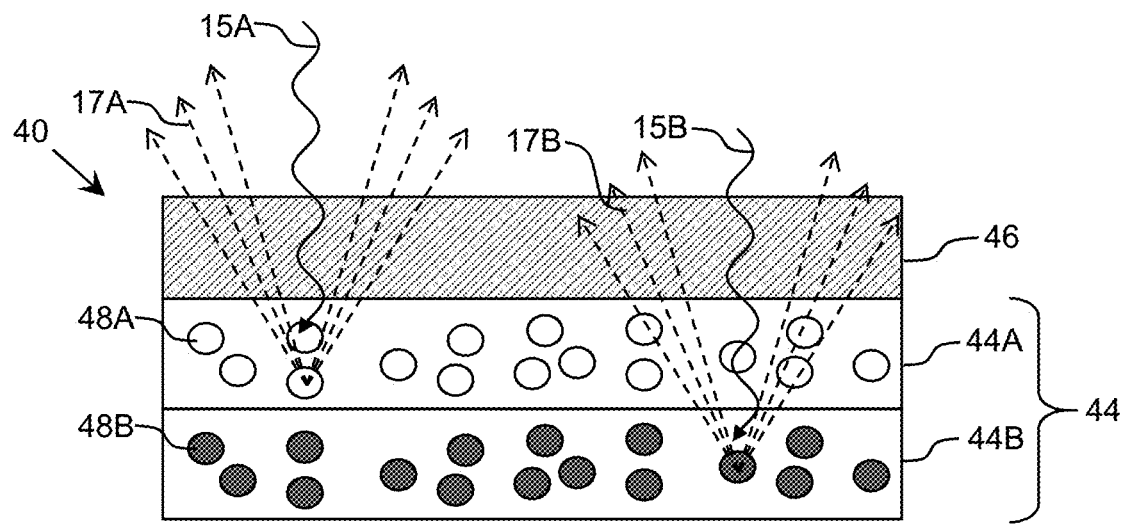
Figure 3B:
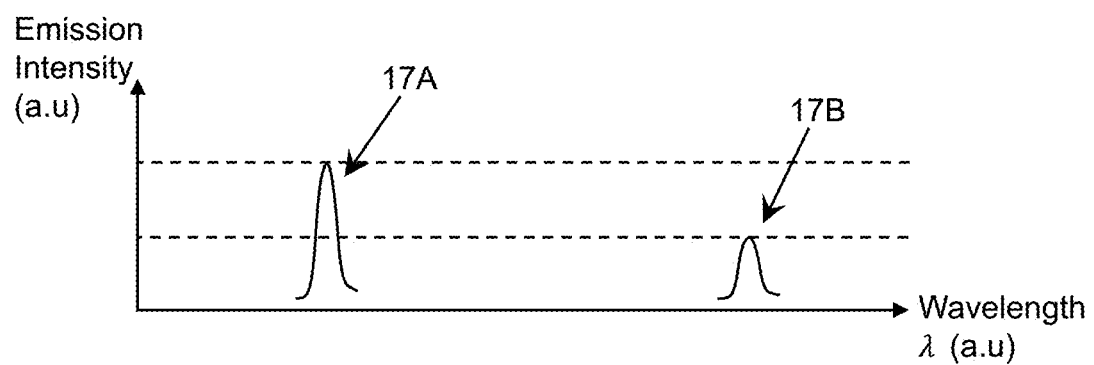
FIG. 3B shows attributes of fluorescent radiation emitted by the light activated region according to an embodiment.

Any combination of one or more of various solutions can be utilized to create fluorescent radiation 17A, 17B with one or more different attributes. For example, FIG. 3A shows a cross-section of another illustrative light activated region 40 according to an embodiment. In this case, the light activated region 40 includes a first layer 44 that includes two sub-layers 44A, 44B. Each sub-layer 44A, 44B can have one or more transmission and/or fluorescent properties that are different from that of the other sub-layer 44A, 44B. For example, as illustrated by FIG. 3B, the fluorescent radiation 17A can have an emission intensity and/or a wavelength that differ from the emission intensity and/or wavelength of the fluorescent radiation 17B.

The different property(ies) of the fluorescent radiation 17A, 17B can be independent of the wavelength of the radiation 15A, 15B. To this extent, the radiation 15A, 15B can be the same, while the fluorescent radiation 17A, 17B have one or more properties that differ from each other. In an embodiment, the properties of the fluorescent radiation 17A, 17B can be wavelength dependent. For example, the sub-layer 44A may be transparent to radiation 15B, but not transparent to the radiation 15A, which can have a wavelength that differs from that of the radiation 15B. In this case, the sub-layer 44B will emit fluorescent radiation 17B when the light activated region 40 is illuminated by the radiation 15B, but not when the light activated region 40 is only illuminated by the radiation 15A. In an embodiment, the sublayer 44A can comprise a thin layer of semiconductor material that has an absorption edge at a wavelength that is higher than the wavelength of the radiation 15A but lower than the wavelength of the radiation 15B. For instance, the layer can comprise an AlGaN film that can have absorption edge at wavelength of 280 nm resulting in absorption of 270 nm radiation and transmission of 290 nm radiation. Other materials can comprise materials with nano-dots and composite materials having semiconductor nano-regions.

The different property(ies) of the fluorescent radiation 17A, 17B can result from differing fluorescent properties of the particles 48A, 48B in each sub-layer 44A, 44B. To this extent, the particles 48A, 48B can have one or more attributes that differ from each other. For example, the particles 48A, 48B can be formed from different materials. Illustrative materials include various types of fluorescent materials, such as florescent phosphors that are used in fluorescent lamps (e.g., $LaPO_4:Ce^{3+}$, $Tb^{3+}$) and/or the like. While each sub-layer 44A, 44B is shown including only one type of particles, it is understood that a sub-layer or a layer described herein can include any number of different types of particles. To this extent, while two different particles are shown included in two separate sub-layers, the first layer 44 could comprise a single layer with the particles 48A, 48B interspersed with one another.

Figure 4:
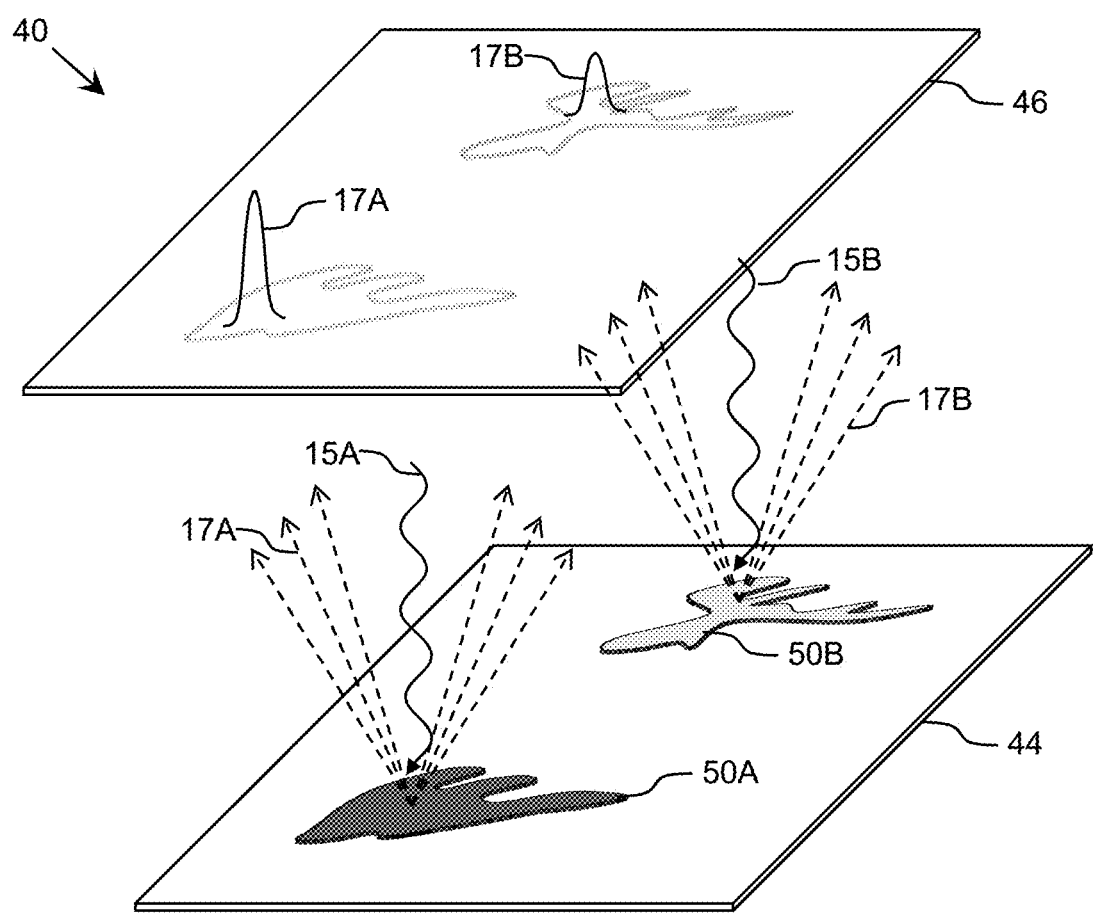
FIG. 4 shows an exploded view of an illustrative light activated region according to an embodiment.

In addition to varying vertically, a light activated region can vary laterally. For example, FIG. 4 shows an exploded view of an illustrative light activated region 40 according to an embodiment. In this case, the first layer 44 includes a first lateral region 50A and a second lateral region 50B, each of which emits fluorescent radiation 17A, 17B in a distinct manner. For example, the fluorescent radiation 17A, 17B can have one or more properties that differ as described herein and as shown schematically in the second layer 46. Alternatively, the fluorescent radiation 17A, 17B can be induced using different ultraviolet radiation 15A, 15B. Regardless, as illustrated, each lateral region 50A, 50B can have a shape of an arbitrary complexity. While the light activated region 40 is shown including two lateral regions 50A, 50B, each of substantially the same shape and size, it is understood that a light activated region can include any number of lateral regions, with the regions having two or more unique sizes and/or shapes. The lateral regions can be formed by, for example, depositing different fluorescent materials in different lateral regions, which can be achieved through printing with fluorescence ink, for example.

Returning to FIG. 1, an article 10 including a light activated region described herein can be authenticated by an authentication environment 11. In particular, the authentication environment 11 can include the data acquisition component 18, which can include an ultraviolet source 14, which illuminates a surface of the article 10 with ultraviolet radiation 15 and a fluorescence sensor 16 that can detect fluorescent radiation 17 emitted by the article 10. The data acquisition component 18 can include any of various configurations for the ultraviolet source 14 and the fluorescence sensor 16, which can be selected based on one or more properties of the article 10 to be authenticated.

Figure 5A:
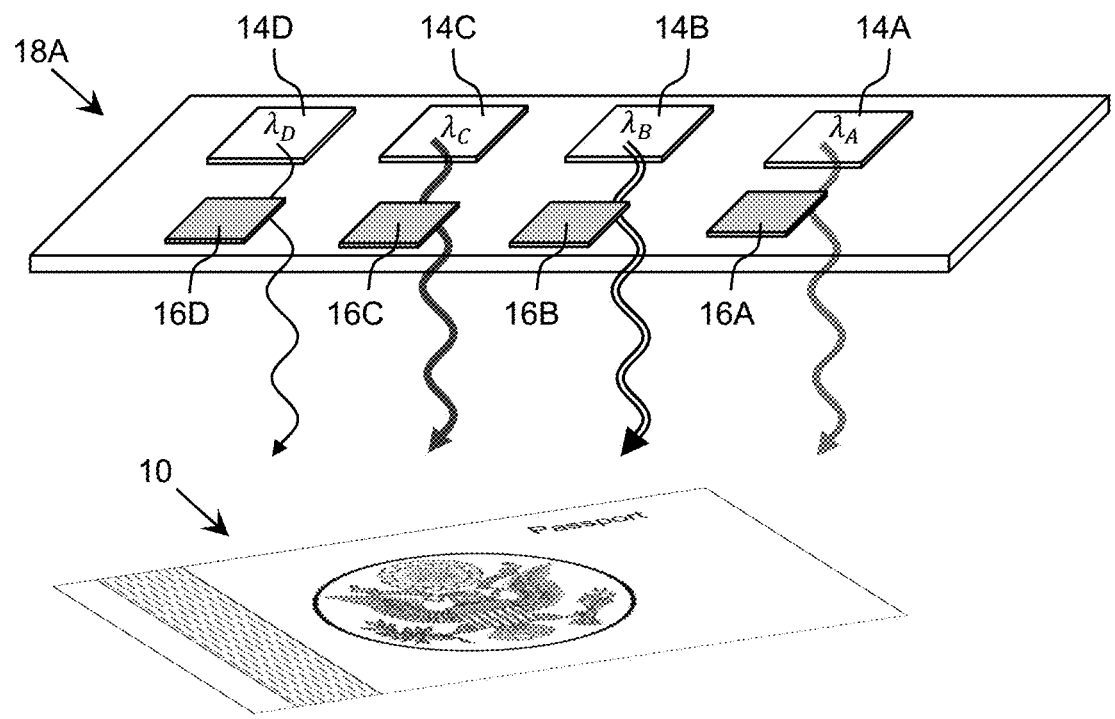
FIGS. 5A-5D show illustrative configurations of data acquisition components according to embodiments.

In an embodiment, one or both of the ultraviolet source 14 and the fluorescence sensor 16 include multiple devices. For example, FIGS. 5A-5D show illustrative configurations of data acquisition components 18A-18D according to embodiments. In FIG. 5A, the data acquisition component 18A is shown including four ultraviolet light emitters 14A-14D and four fluorescence sensors 16A-16D. While the data acquisition component 18A is shown including four of each device, it is understood that this is only illustrative, and a data acquisition component can include any number of one or more of each of the emitters and sensors. Similarly, while the emitters 14A-14D and sensors 16A-16D are shown arranged linearly, other arrangements for the emitters 14A-14D and sensors 16A-16D can be utilized.

Regardless, an ultraviolet light emitter 14A-14D can be, for example, an ultraviolet light emitting diode. The ultraviolet light emitted by each ultraviolet light emitter 14A-14D can have a corresponding peak wavelength and a corresponding width (as measured by the full width at half maximum) of the ultraviolet light emitted therefrom. In an embodiment, the ultraviolet light emitters 14A-14D emit ultraviolet radiation having multiple distinct peak wavelengths (e.g., as illustrated by $\lambda_A$-$\lambda_D$). In an embodiment, each peak wavelength is separated from the other peak wavelengths by at least the width of the light emitted by the corresponding ultraviolet light emitter(s) 14A-14D. Similarly, the fluorescence sensors 16A-16D can be sensitive to fluorescent radiation of multiple different peak fluorescent wavelengths.

The computer system 20 (FIG. 1) can operate the ultraviolet light emitters 14A-14D and/or the fluorescent sensors 16A-16D individually, in sub-groups, or as a group. Furthermore, the computer system 20 can adjust one or more attributes of the light emitted by the ultraviolet light emitters 14A-14D over time. For example, the computer system 20 can vary an intensity of the ultraviolet radiation over time using any solution (e.g., pulsed operation). The fluorescence sensors 16A-16D can acquire data that enables the computer system 20 to evaluate the magnitude of fluorescence as a function of time for a time varying fluorescent radiation source. For a periodically operating fluorescent radiation source, the fluorescence sensors 16A-16D can acquire data that enables the computer system 20 to evaluate the time shift of the fluorescent peak and the intensity of such peak. Additionally, the ultraviolet light emitters 14A-14D can be configured to emit ultraviolet light in different directions and/or the fluorescence sensors 16A-16D can be configured to sense fluorescent radiation from different directions. In an embodiment, one or more of the ultraviolet light emitters 14A-14D and/or the fluorescence sensors 16A-16D can be configured for movement having one or more degrees of freedom, such as rotational and/or translational degrees of freedom, and the computer system 20 can adjust the direction of the ultraviolet radiation emitted therefrom and/or the fluorescent radiation sensed thereby.

As shown in FIG. 5A, the ultraviolet light emitters 14A-14D can be located adjacent to the fluorescence sensors 16A-16D on the same side of the article 10 to be authenticated. Such a configuration is beneficial when the fluorescent radiation is emitted primarily from the same surface from which the article 10 was illuminated. In an embodiment illustrated in FIG. 5B, the data acquisition component 18B can include a set of ultraviolet light emitters 14A-14D located on a first side of an article 10 to be authenticated and a set of fluorescence sensors 16A-16D located on an opposite side of the article 10. Such a configuration can be beneficial, for example, when the article 10 is transparent to some or all of the ultraviolet radiation emitted by the ultraviolet light emitters 14A-14D.

Figure 5B:
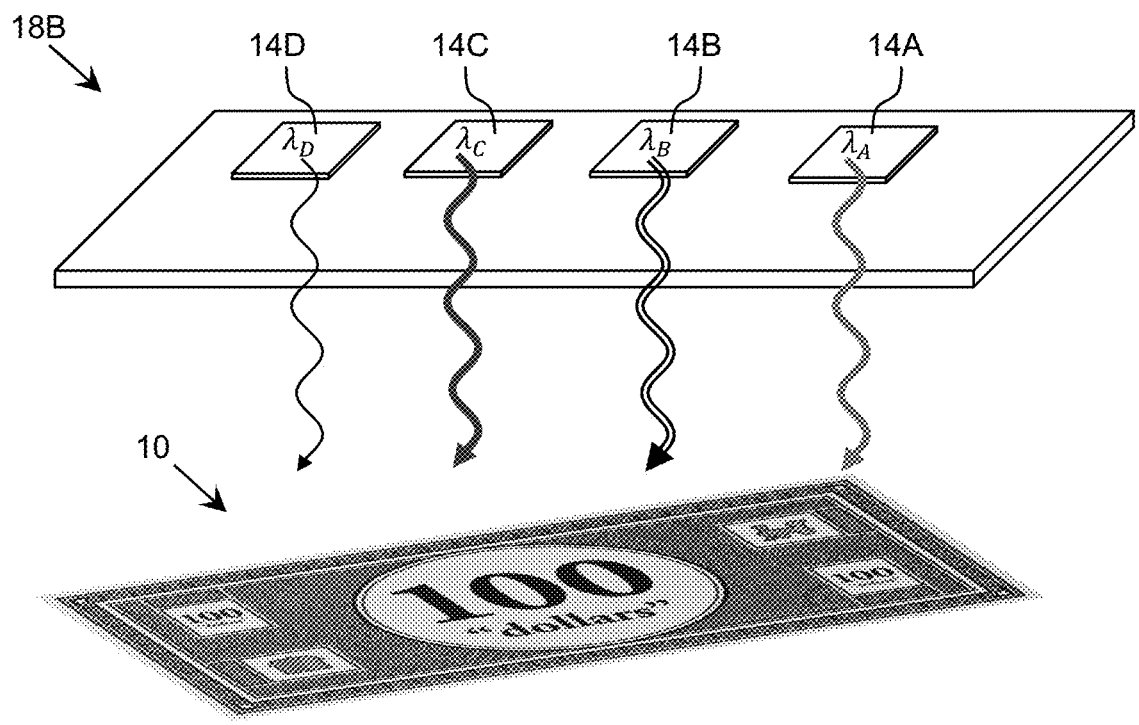
Figure 5B:
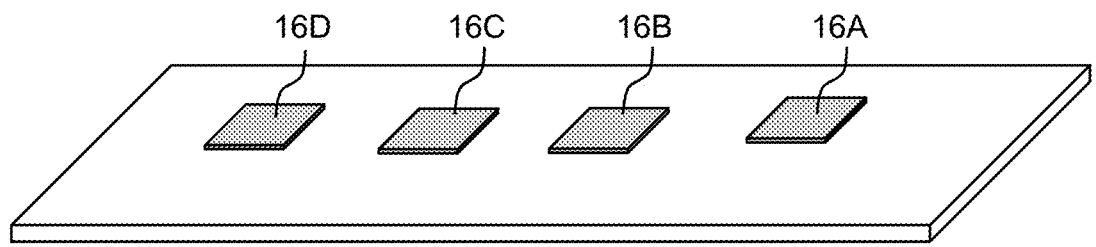

While the detectors 16A-16D are shown only located on one side of the article 10 in FIGS. 5A and 5B, it is understood that the embodiments shown in FIGS. 5A and 5B can be readily combined to include one or more detectors located on both sides of the article. In this case, the particular sensitivity of the detector(s) on each side of the article can be selected based on the radiation to which the article is transparent and the properties of fluorescent radiation emitted by an authentic article.

Additionally, while the discussion has been primarily directed to ultraviolet light and fluorescence, it is understood that embodiments of an authentic article 10 can include one or more regions with features detectable using other radiation, such as infrared radiation, visible light radiation, and/or the like. Such detection can be through the use of any combination of one or more of: reflection, transparency, induced emission, and/or the like. For example, an authentic article 10 can include a watermark, a region with an infrared-sensitive chemical, and/or the like. In an embodiment, a light activated region of an authentic article can include a layer formed of material(s) sensitive to non-ultraviolet radiation, such as infrared radiation, visible radiation, and/or the like. For example, the materials can comprise an infrared fluorescent dye, such as fluorophores: Cy7, Cy7.5, etc.

To this extent, an embodiment of a data acquisition component 18 (FIG. 1) described herein can include one or more sources of other non-ultraviolet radiation, such as an infrared source, a visible light source, and/or the like, and/or one or more corresponding detectors, such as an infrared camera, a visible camera, and/or the like. In this case, each radiation source can emit broadband or narrow band radiation and each detector can be selected to be sensitive to the corresponding radiation emitted by an authentic article 10. The various functionality and features described in conjunction with the ultraviolet source 14 and the fluorescence detector 16 can be applied to the source(s) and detector(s) for the other types of radiation.

Figure 5C:
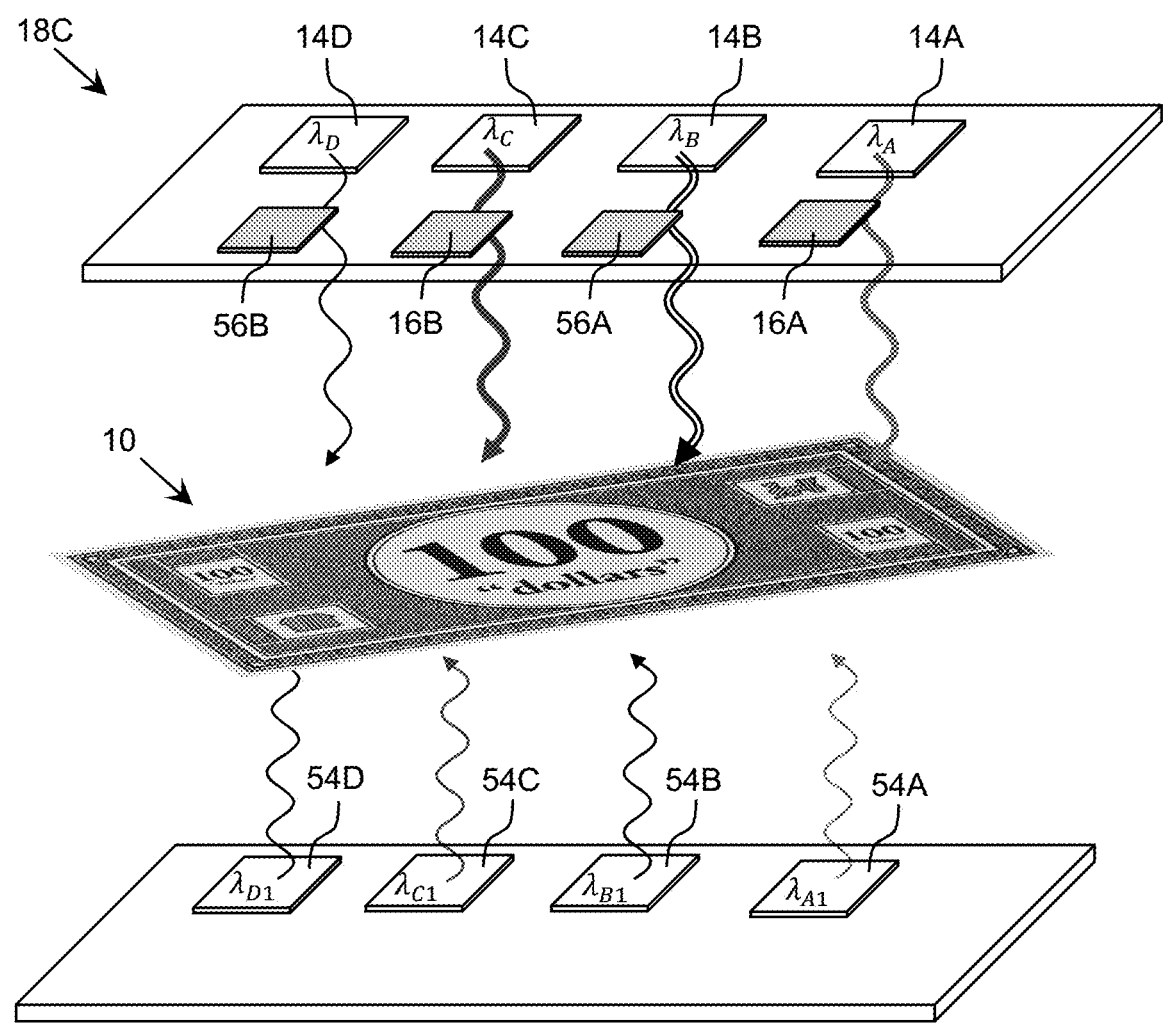

FIG. 5C shows an illustrative data acquisition component 18C including multiple types of radiation sources and multiple types of detectors according to an embodiment. In this case, an article 10 to be authenticated can be placed such that ultraviolet light emitters 14A-14D illuminate a first side of the article and other light emitters 54A-54D (e.g., visible light emitters or infrared light emitters) illuminate an opposite side of the article. Fluorescence detectors 16A, 16B and other detectors 56A, 56B can be located on the first side of the article. In this configuration, the computer system 20 (FIG. 1) can operate the ultraviolet light emitters 14A-14D to emit ultraviolet light which causes a light activated region of an authentic article 10 to emit fluorescent radiation, which can be detected by the fluorescence detectors 16A, 16B. Additionally, the computer system 20 can operate the other light emitters 54A-54D to emit other radiation, which can result in one or more properties of the article 10 (e.g., fluorescence, watermark, etc.) being sensed by the other detectors 56A, 56B and/or the fluorescence detectors 16A, 16B. While the data acquisition component 18C is shown including all of the detectors on the first side of the article 10 and only emitters of one type on each side of the article 10, it is understood that this is only illustrative and embodiments of the data acquisition component 18C can include various combinations of detectors and/or emitters located on either side of the article 10.

Figure 5D:
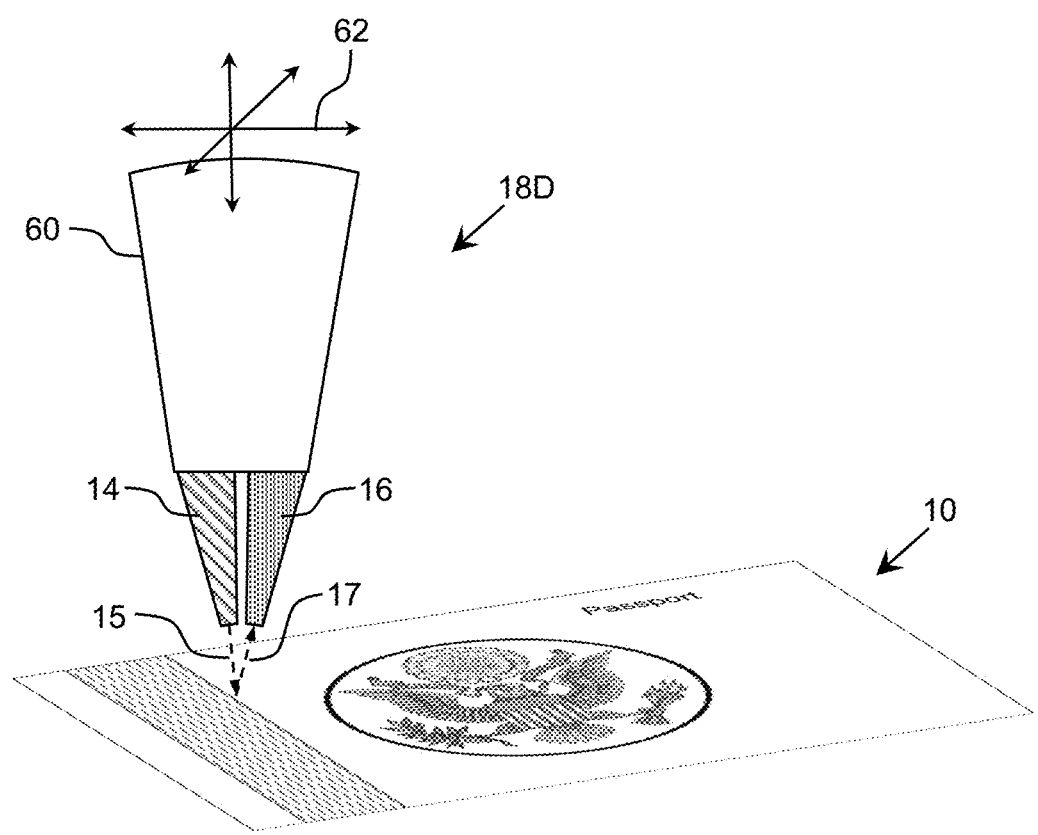

As shown in FIG. 5D, the data acquisition component 18D can include a support structure 60 to which both the ultraviolet source 14 and fluorescence detector 16 are attached. The computer system 20 (FIG. 1) can operate the support structure 60 to move the support structure 60 in various lateral and/or vertical directions as indicated by the range of motions 62. While not shown, it is understood that an embodiment of the support structure 60 also can enable rotational movement of thereof. In this case, the support structure 60 can enable the ultraviolet source 14 and fluorescence detector 16 to be utilized to scan a light activated region of an authentic article 10 in a lateral direction. For example, such functionality can be useful when the light activated region is inhomogeneous in the lateral direction. In addition to moving the ultraviolet source 14 and fluorescence detector 16, an embodiment of the ultraviolet source 14 can be configured to emit ultraviolet light of different peak wavelengths, which the computer system 20 can selectively use when analyzing different portions of the light activated region of the authentic article 10. While not shown for clarity, it is understood that the support structure 60 also can support additional sources and/or detectors described herein. Additionally, an embodiment of the data acquisition component 18D can include more than one support structure 60, which can be located on the same or different sides of the article 10, each of which can be independently configured and operated by the computer system 20.

While shown and described herein as an article configured for authentication using ultraviolet light and fluorescent radiation and a corresponding system for performing such authentication, it is understood that aspects of the invention further provide various alternative embodiments. For example, in one embodiment, the invention provides a computer program fixed in at least one computer-readable medium, which when executed, enables a computer system to authenticate an article by performing a process described herein. To this extent, the computer-readable medium includes program code, such as the authentication program 30 (FIG. 1), which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; and/or the like.

In another embodiment, the invention provides a method of providing a copy of program code, such as the authentication program 30 (FIG. 1), which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for authenticating an article by performing a process described herein. In this case, the generating can include configuring a computer system, such as the computer system 20 (FIG. 1), to implement a process of authenticating an article described herein. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

As used herein, unless otherwise noted, the term "set" means one or more (i.e., at least one) and the phrase "any solution" means any now known or later developed solution. The singular forms "a," "an," and "the" include the plural forms as well, unless the context clearly indicates otherwise. Additionally, the terms "comprises," "includes," "has," and related forms of each, when used in this specification, specify the presence of stated features, but do not preclude the presence or addition of one or more other features and/or groups thereof.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. An article comprising:
   a light activated region having a fluorescence signature with a plurality of attributes enabling authentication of the article, the light activated region comprising:
   a first layer including a plurality of particles, wherein the plurality of particles are configured to emit fluorescent radiation in response to being radiated with ultraviolet radiation, wherein the first layer includes:
      a first sub-layer including a first plurality of nanoparticles of a first composition; and
      a second sub-layer adjacent to the first sub-layer, the second sub-layer including a second plurality of nanoparticles of a second composition distinct from the first composition; and
   a second layer immediately adjacent to the first layer, wherein the second layer is transparent to both the fluorescent radiation and the ultraviolet radiation and is stable and inert to an ambient environment within which the article is configured for use.

2. The article of claim 1, wherein the article further includes a substrate storing information, and wherein the first layer is located between the substrate and the second layer.

3. The article of claim 2, wherein the light activated region is located only over a portion of a surface of the substrate.

4. The article of claim 1, wherein the article is one of: currency, a payment card, or a government-issued identification card.

5. The article of claim 1, wherein the article is one of: artwork or a legal document.

6. The article of claim 1, wherein the second layer comprises a fluoropolymer.

7. The article of claim 1, wherein the light activated region includes a plurality of distinct lateral regions, each lateral region having a distinct fluorescence signature.

8. The article of claim 1, wherein the plurality of particles include fluorescent nanoparticles.

9. An authentication system comprising:
   a data acquisition component including:
      an ultraviolet source;
      a fluorescence sensor; and
      at least one other light source configured to emit at least one of: infrared radiation or visible light; and
   means for authenticating an article using the data acquisition component, wherein the means for authenticating performs the acts of:
      illuminating a surface of the article with ultraviolet radiation emitted by the ultraviolet source, the ultraviolet radiation having a first set of properties;
      acquiring, using the fluorescence sensor, fluorescence data corresponding to fluorescence emitted from the article in response to the illuminating;
      further illuminating the surface of the article with at least one of: infrared radiation or visible light emitted from the at least one other source;
      acquiring, using at least one of: the fluorescence sensor or another sensing device, appearance data corresponding to the appearance of the article in response to the further illuminating; and
      evaluating an authenticity of the article using the fluorescence data corresponding to the fluorescence and the appearance data corresponding to the appearance of the article, and
   wherein an authentic article comprises an appearance and fluorescence formed by:
      a substrate storing information; and
      a light activated region located on at least a portion of a first surface of the substrate, the light activated region including:
         a first layer including a plurality of particles, wherein the plurality of particles are configured to emit fluorescent radiation in response to being radiated with ultraviolet radiation; and
         a second layer immediately adjacent to the first layer to control properties of the fluorescent radiation emitted from the first layer and properties of the ultraviolet radiation that irradiates the first layer, wherein the second layer is distinct from the first layer, and wherein the second layer is transparent to both the fluorescent radiation and the ultraviolet radiation.

10. The system of claim 9, wherein the ultraviolet source includes a first set of ultraviolet light emitting diodes configured to emit the ultraviolet radiation having the first set of properties.

11. The system of claim 10, wherein the ultraviolet source includes a second set of ultraviolet light emitting diodes configured to emit ultraviolet radiation having a second set of properties different from the first set of properties, and wherein the means for authenticating further performs the acts of:

illuminating the surface of the article with ultraviolet radiation having the second set of properties; and acquiring, using the fluorescence sensor, data corresponding to fluorescence emitted from the article in response to the illuminating with the ultraviolet radiation having the second set of properties, wherein the evaluating further uses the data corresponding to the fluorescence emitted from the article in response to the illuminating with the ultraviolet radiation having the second set of properties.

12. The system of claim 9, wherein the ultraviolet source emits ultraviolet radiation having a spectrum with a full width at half maximum of less than one hundred nanometers.

13. The system of claim 9, wherein the data acquisition component further includes a support structure supporting the ultraviolet source and the fluorescence sensor, and wherein the means for authenticating further performs the act of moving the support structure with respect to a surface of the article during the illuminating and acquiring.

14. The system of claim 9, wherein the evaluating an authenticity of the article includes comparing the acquired fluorescence data and the appearance data to a target signature having data defining acceptable target fluorescence data and appearance data.

15. A system for authenticating an article, the system comprising:
  an article configured for authentication using a fluorescence signature emitted in response to ultraviolet light, the article including:
    a substrate storing information; and
    a light activated region located on at least a portion of a first surface of the substrate, the light activated region including:
      a first layer including a plurality of particles, wherein the plurality of particles are configured to emit fluorescent radiation in response to being radiated with ultraviolet radiation; and
      a second layer immediately adjacent to the first layer to control properties of the fluorescent radiation emitted from the first layer and properties of the ultraviolet radiation that irradiates the first layer, wherein the second layer is distinct from the first layer, and wherein the second layer is transparent to both the fluorescent radiation and the ultraviolet radiation, and is stable and inert to an ambient environment within which the article is configured for use.

16. The system of claim 15, wherein the light activated region includes a plurality of distinct lateral regions each with a plurality of particles configured to emit fluorescent radiation, each lateral region occupying a different position in the light activated region, with each lateral region having a distinct fluorescence signature.

17. The system of claim 15, wherein the plurality of particles includes:
  a first plurality of fluorescent nanoparticles having a first fluorescence signature; and
  a second plurality of fluorescent nanoparticles having a second fluorescence signature distinct from the first fluorescence signature.

18. The system of claim 15, further comprising:
  a data acquisition component including:
    an ultraviolet source for generating the ultraviolet radiation; and
    a fluorescence sensor for acquiring data corresponding to fluorescent radiation emitted by the light activated region; and
  means for authenticating the article using the data acquisition component, wherein the means for authenticating performs the acts of:
    illuminating at least a portion of the light activated region with ultraviolet radiation emitted by the ultraviolet source;
    acquiring, using the fluorescence sensor, data corresponding to fluorescent radiation emitted from the article in response to the illuminating; and
    evaluating an authenticity of the article using the data corresponding to the fluorescent radiation.

19. The system of claim 18, wherein the data acquisition component further includes a support structure supporting the ultraviolet source and the fluorescence sensor, and wherein the means for authenticating further performs the act of moving the support structure with respect to a surface of the article during the illuminating and acquiring.

20. The system of claim 15, wherein the second layer is configured to control at least one of: an intensity and/or distribution of the fluorescent radiation emitted from the light activated region, or transparent properties of the ultraviolet radiation and/or the fluorescent radiation.

* * * * *